(12) United States Patent
Silver

(10) Patent No.: US 6,423,030 B1
(45) Date of Patent: Jul. 23, 2002

(54) LUBRICATED BREASTSHIELD

(75) Inventor: Brian H. Silver, Cary, IL (US)

(73) Assignee: Medela Holding AG (CH)

( * ) Notice: Subject to any disclaimer, the term of this patent is extended or adjusted under 35 U.S.C. 154(b) by 0 days.

(21) Appl. No.: 09/723,168

(22) Filed: Nov. 27, 2000

(51) Int. Cl.$^7$ ............................................... A61M 1/06
(52) U.S. Cl. ........................................................ 604/74
(58) Field of Search ..................................... 604/73–76

(56) References Cited

U.S. PATENT DOCUMENTS

| | | | | |
|---|---|---|---|---|
| 3,977,405 A | * | 8/1976 | Yanase | 604/74 |
| 4,323,067 A | * | 4/1982 | Adams | 604/74 |
| 4,857,051 A | | 8/1989 | Larsson | 604/74 |
| 4,929,229 A | | 5/1990 | Larsson | 604/74 |
| 5,281,229 A | * | 1/1994 | Neward | 606/123 |
| 5,355,832 A | | 10/1994 | Loh et al. | 118/723 |
| 5,447,799 A | | 9/1995 | Loh et al. | 428/448 |

OTHER PUBLICATIONS

EM Corporation, Parylene Coating Services Brochure, West Lafayette, IN.

Speedline Technologies, Specialty Coating Systems—Parylene Overview, May 1, 2000, http://www.scscookson.com/parylene/.

Advanced Surface Technology, Product Overview—ParyLAST, Apr. 19, 2000, http://www.astp.com/ast_parylast.html.

Hydromer, Hydromer Medical Coatings, Aug. 10, 2000, http://www.hydromer.com.

GLS Corporation, Technical Data Sheet Kraton G2705 Thermoplastic Rubber Compound Brochure, Cary, Illinois.

Coating Technologies, Inc., Lubricoat Brochure, Scotch Plains, NJ.

Witco Corporation, Kemamide E Ultra Brochre, Greenwich, CT.

* cited by examiner

*Primary Examiner*—Sharon Kennedy
(74) *Attorney, Agent, or Firm*—Baniak Pine & Gannon

(57) ABSTRACT

An improved breastshield for a breastpump having a coating of a lubricating material formed integral with the breastshield.

12 Claims, 1 Drawing Sheet

LUBRICATED BREASTSHIELD

FIELD OF THE INVENTION

The invention relates to breastshields used with breastpumps by nursing mothers.

BACKGROUND OF THE INVENTION

Breastshields typically used in conjunction with breastpumps have a conical configuration and are usually funnel-shaped. The breastshield need not be conical, of course, but nonetheless will ordinarily have a part within which at least some of the breast is received along with the nipple. In use, the interior of the breastshield is placed against the nursing mother's breast, and the breastpump extracts milk from the breast through application of a negative pressure (vacuum) within the breastshield. Breastpumps having breastshields of this type are shown and described in U.S. Pat. Nos. 4,929,229 and 4,857,05 1, for instance.

Breastshields typically have a funnel-shape, comprising a conical portion with a tubular extension, sometimes referred to as the nipple tunnel. The nipple and surrounding breast are received in the conical portion, with the nipple often extending into the tubular extension. Under vacuum, the breast is pulled further into the breastshield, ordinarily with the nipple then being pulled into the tubular extension, with the surrounding breast thereby also compressed about the nipple.

A nursing mother's nipples may thus be forced against the wall of the nipple tunnel under vacuum. This may cause friction against the wall as the nipple moves deeper into the nipple tunnel. There can also be friction between the breast and the conical portion, as well as the nipple tunnel. This may result in irritation, particularly if the mother is already suffering from some topical problem, such as a chapped or cracked nipple condition. This makes the pumping of milk from the breast uncomfortable. If it were possible to reduce or eliminate the chafing and irritation of a nursing mother's breast when a breastpump is used, an advance in the art would be afforded.

SUMMARY OF THE INVENTION

The invention comprises an improved breastshield for a breastpump having a breast-receiving portion which is provided with a lubricious surface. In one embodiment, it has bonded to its interior breast-contacting surface a coating of a polymeric lubricant, having a reduced coefficient of friction. The polymeric lubricant may preferably be from the group consisting of polytetrafluoroethylene, fluorinated ethylene-propylene copolymers, poly (vinylidine fluoride), polyparaxylene and silicone lubricant polymers. Preferred polymers of this group are the polyparaxylene polymers and the polytetrafluoroethylene polymers, with parylene being a presently preferred lubricating material. It is to be understood that any number of other well-known lubricating materials may be used in the practice of the invention, as will be made evident hereafter. Due to the particular application of the invention as a breast shield, it is necessary that the particular polymers chosen be acceptable for bodily contact.

While the lubricating material may be bonded directly to a rigid breast-receiving part of the breastshield, which could also be an insert or adaptor received in a breastshield, it is furthermore envisioned to provide the lubricious surface in conjunction with elastomeric materials making up a soft breast-receiving part. Whether a rigid or softer substrate is employed, the lubricating material can be provided as a coating to the already formed substrate (or base). Alternatively, the two layers could be molded together in the same molding operation, or in a two-shot type molding process, just to name two other applications.

In another embodiment, the lubricant polymer material is mixed with or otherwise contained within the substrate, to provide a relatively homogeneous lubricant-containing breastshield surface area.

Yet another variation of the foregoing embodiment has the lubricant material releasable upon contact with water, or heat. The lubricant may be encapsulated, for instance, and then released to coat the surface in use.

The foregoing objectives and advantages of the invention will be further understood upon consideration of the following detailed description of certain embodiments taken in conjunction with the drawings, in which:

BRIEF DESCRIPTION OF THE DRAWINGS

In the drawings, like parts have like numbers.

DETAILED DESCRIPTION OF EMBODIMENTS OF THE INVENTION

Figure 1:
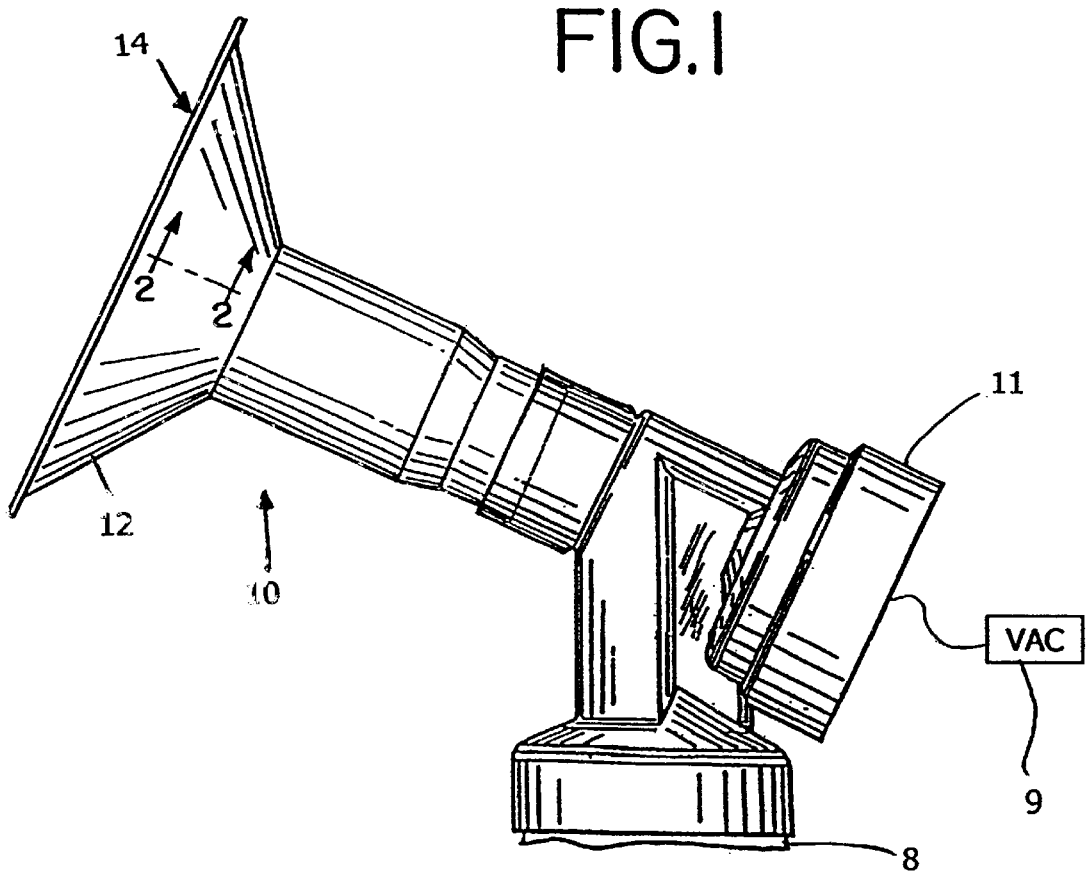
FIG. 1 is a funnel-shaped breastshield having an interior lubricated surface.

With respect to the drawings, there is shown in FIG. 1 a funnel-shaped breastshield 10 having a breast-receiving cone 12, the interior of which is designated by the numeral 14. This is a relatively well-known type of breastshield, having a rigid plastic construction. It will be understood, however, that the application of this invention is not limited to just such a form of the breastshield.

The breastpump assembly which includes the breastshield 10 further has a container 8 for collecting milk, and source of pressure, typically a vacuum (negative pressure), schematically indicated at 9. The vacuum source 9 would typically be a manually operated piston pump attached at collar 11, a battery operated diaphragm pump attached at collar 11, a house-current driven vacuum pump using a vacuum line (tube) attached to a port within the collar 11, among others. Again, reference can be made to U.S. Pat. Nos. 4,929,229 and 4,857,051 for such detail. The invention herein is, however, not limited to the manner in which the breast is manipulated for the expression of milk.

Figure 2A:
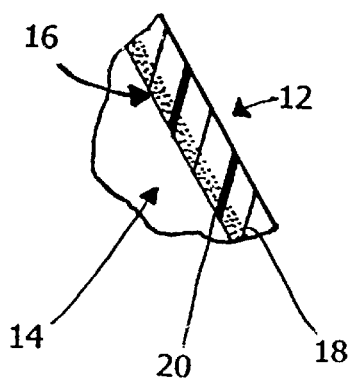
FIGS. 2a and 2b are two embodiments of the invention each taken across the lines 2—2 of FIG. 1.
Figure 2B:
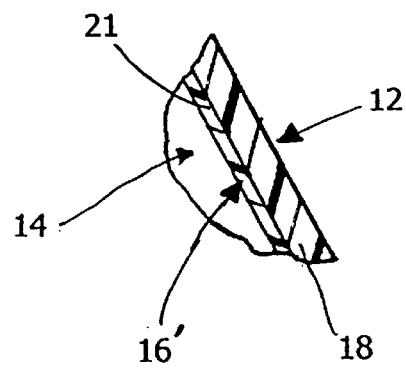

FIGS. 2a and 2b show a lubricating area formed integral with the interior 14 of the main breast-receiving portion of cone 12. As shown in FIG. 2a, the area 16 is part of a base polymer 18 forming the general structure of the cone 12. Distributed about its interior surface and partially dispersed therein is a lubricant polymer in the form of intermingling particles 20, which are encapsulated for release in use.

FIG. 2b shows a different embodiment from 2a, wherein a lubricious coating 16' is provided in the form of a discrete layer 21, such as one yielded through coating base polymer 18 with the lubricating material. This can be any number of lubricants, including but not limited to a dry lubricant material which reduces friction on contact with liquid.

The layer 21, in the form of a film, may be bonded by any suitable means. One particular lubricious material considered advantageous is parylene. A coating thickness in the range from about 1500 to about 2500 Angstroms may suffice. One type of parylene considered suitable is provided under the name ParyLAST, by AST Products, Inc. of Billerica, Mass. (see U.S. Pat. Nos. 5,355,382 and 5,447, 799), and can be applied to a silicone substrate. Another lubricating material considered applicable is a coating material sold under the name HYDROMER by a company of the same name, and is a polyvinyl pyrrolidone interacted with an isocyanate prepolymer.

As indicated, it is possible to employ a single lubricating polymeric material to accomplish the goals of the invention. To effectuate the desired lower coefficients of friction, it is also possible to blend a variety of polymers, such as silicone polymers with fluorinated polymers with the lubricating material.

An elastomeric polymer considered useful as the substrate is KRATON G2705, a thermoplastic elastomer that is a block copolymer, having a synthetic rubber base and terminal polystyrene moieties. This polymer has been approved for use in medical devices. This product is available from GLS Corporation of Cary, Ill. It typically has the following physical properties:

| | |
|---|---|
| Hardness, Shore A, (ASTM D2240) injection molded | 57 |
| Specific Gravity, (D792) | 0.90 |
| Tensile Modulus at 300% Elongation, PSI, (D412) In Flow Direction | 405 |
| Tensile Strength at Break, PSI, (D412) In Flow Direction | 970 |
| Percent Elongation at Break | 655 |
| Tear Strength, PLI, Die C, (D624) In Flow Direction | 136 |
| Color | Translucent |

It should be noted that this product by itself has little lubricity. Another useful lubricant polymer additive that could be applied to a Kraton G2705 base is a proprietary material sold under the trade name LUBRICOAT, by Coating Technologies Inc. of Scotch Plaines, N.J. This material has an exceptionally low coefficient of friction.

Yet another lubricant that has been considered is sold by Witco Corporation of Greenwich, Conn. under the name KENAMIDE E ULTRA, and is an unsaturated fatty monamide derived from erucic acid. The material may be blended with the plastic making up the surface layer of the breastshield, for one example. KENAMIDE E ULTRA has the following specifications:

| | |
|---|---|
| Amide Content, % | 98.0 min. |
| Erucic Content, % by GLC | 90.0 min. |
| Color, Gardner (1963) | 2 max. |
| Acid Value | 1 max. |
| Iodine Value | 71–76 |
| Melting Point, ° C. (° F.) | 76–86 (168–187) |
| Moisture, % | 0.25 max. |

Thus, while the invention has been described with respect to certain presently preferred embodiments, those with skill in the art will recognize changes, modifications and other applications which will fall within the scope of the inventive concepts and claims.

What is claimed is:

1. An improved breastshield for a breastpump having a breast-receiving part within which a portion of a mother's breast is received including the nipple, wherein the improvement comprises: a lubricious surface formed integral with the breast-receiving part.

2. The improved breastshield of claim 1, wherein the lubricious surface layer is a polymeric material from the group consisting of polytetrafluoroethylene, fluorinated ethylene-propylene copolymers, poly(vinylidine fluoride), polyparaxylene and silicone lubricant polymers.

3. The improved breastshield of claim 1, where the lubricious surface layer is parylene.

4. The improved breastshield for the breastpump of claim 1, wherein the lubricious surface layer is intermingled with a non-lubricating base layer.

5. The improved breastshield of claim 2, wherein the polymeric material is coated on the surface of a base layer forming the structure of the breast-receiving part.

6. The improved breastshield of claim 1, wherein a lubricant material is dispersed within a substrate and encapsulated therein for release in use of the breastshield.

7. An improved breastpump comprising a breastshield having an interior portion adapted to receive at least part of a mother's breast including the nipple therein;

a container communicating with said breastshield to receive milk;

a pressure source communicating with said interior portion to manipulate the breast therein for the expression of milk; and a lubricious surface formed integral with said interior portion.

8. The improved breastpump of claim 7, wherein said lubricious surface is a lubricant coating forming an outer layer to said interior portion.

9. The improved breastpump of claim 7, wherein said lubricious surface is a lubricant material which is intermingled with a non-lubricating base layer.

10. The improved breastpump of claim 9, wherein said lubricant material is dispersed within a substrate and encapsulated therein for release in use of the breastshield.

11. An improved breastshield for a breastpump having a breast-receiving part within which a portion of a mother's breast is received including the nipple, wherein the improvement comprises: a lubricious surface bonded to a major portion of the breast-receiving part.

12. The improved breastshield of claim 11, wherein the entire breast-receiving portion includes the lubricious surface.

* * * * *

UNITED STATES PATENT AND TRADEMARK OFFICE
CERTIFICATE OF CORRECTION

PATENT NO. : 6,423,030 B1
DATED : July 23, 2002
INVENTOR(S) : Silver

It is certified that error appears in the above-identified patent and that said Letters Patent is hereby corrected as shown below:

<u>Column 2,</u>
Lines 67, "5,355,382" should read -- 5,355,832 --.

<u>Column 4,</u>
Lines 8-9, "with the" should read -- with a major portion of the --.
Lines 11, 16 and 18, "surface layer is" should read -- surface is --.
Line 15, "1, where the" should read -- 1, wherein the --.
Line 35, "with said" should read -- with a major portion of said --.

Signed and Sealed this

Eighteenth Day of May, 2004

JON W. DUDAS
*Acting Director of the United States Patent and Trademark Office*